United States Patent [19]
Kambara et al.

[11] Patent Number: 6,132,578
[45] Date of Patent: Oct. 17, 2000

[54] METHOD AND APPARATUS FOR ELECTROPHORESIS SEPARATION AND DETECTION

[75] Inventors: Hideki Kambara, Hachioji; Keiichi Nagai, Higashiyamato; Hiroaki Machida, Saitama-ken, all of Japan

[73] Assignees: Hitachi, Ltd.; Hitachi Electronics Engineering Co., Ltd., both of Tokyo, Japan

[21] Appl. No.: 08/880,544

[22] Filed: Jun. 23, 1997

[30] Foreign Application Priority Data

Jun. 28, 1996 [JP] Japan ................................. 8-168977

[51] Int. Cl.[7] .................................................. G01N 27/26
[52] U.S. Cl. ........................ 204/451; 204/452; 204/603; 204/612; 356/344
[58] Field of Search ..................... 204/461, 600; 7/612, 452, 603, 450; 356/344

[56] References Cited

U.S. PATENT DOCUMENTS

| | | | |
|---|---|---|---|
| 4,832,815 | 5/1989 | Kambara et al. | 204/612 |
| 5,062,942 | 11/1991 | Kambara et al. | 204/612 |

(List continued on next page.)

FOREIGN PATENT DOCUMENTS

| | | |
|---|---|---|
| 61-44353 | 3/1986 | Japan . |
| 1-116441 | 5/1989 | Japan . |

(List continued on next page.)

OTHER PUBLICATIONS

Ju et al. ("Design and Synthesis of Fluorescence Energy transfer Dye–Labeled primers and their Application fro DNA Sequencing and analysis", Analytical Biochemistry 231, 131–140 (Oct. 1995)).

Th. Förster, "Zwischenmolekulare Energiewanderung und Fluoreszenz", *Annalen der Physik*, vol. 2, No. 6, pp. 55–75, 1948 (in German), month unknown.

L. Stryer et al., "Energy Transfer: A Spectroscopic Ruler", *Proceedings of the National Academy of Sciences*, vol. 58, pp. 719–726, 1967, month unknown.

J. Prober et al., "A System for Rapid DNA Sequencing with Fluorescent Chain–Terminating Dideoxynulceotides", *Science*, vol. 238, Oct. 16, 1987, pp. 336–341, month unknown.

J. Ju et al., "Design and Synthesis of Fluorescence Energy Transfer Dye–Labeled Primers and Their Application for DNA Sequencing and Analysis", *Analytical Biochemistry*, vol. 231, pp. 131–140, Oct. 10, 1995.

*Primary Examiner*—Jill Warden
*Assistant Examiner*—Alex Noguerda
*Attorney, Agent, or Firm*—Antonelli, Terry, Stout & Kraus, LLP

[57] ABSTRACT

An electrophoresis separation and detection apparatus for separating and detecting fluorophore-labeled samples by electrophoresis, which comprises a migrating and separating means for electrophoresis separation of the samples labeled with two or more kinds of fluorophore labels, respectively; an irradiating means which casts two or more kinds of exciting lights having different wavelengths on a plurality of positions in all the electrophoresis lanes or on the extensions of all the electrophoresis lanes substantially at the same time; and a detecting means which detects the samples separated by the electrophoresis, at the positions on which the exciting lights are casted, wherein each fluorophore label is composed of a substance for excitation which is excited by the exciting light and a substance for emission which emits light owing to energy transfer from the substance for excitation; two or more kinds of substances are used as each of the substance for excitation and the substance for emission; and the detecting means detects the samples by distinguishing the two or more kinds of the fluorophore labels from one another on the basis of the difference of combination of the two or more kinds of the substances used as the substance for excitation and those used as the substance for emission.

28 Claims, 6 Drawing Sheets

U.S. PATENT DOCUMENTS

| | | | |
|---|---|---|---|
| 5,162,654 | 11/1992 | Kostichka et al. | 250/458.1 |
| 5,192,412 | 3/1993 | Kambara et al. | 204/612 |
| 5,277,780 | 1/1994 | Kambara | 204/603 |
| 5,307,148 | 4/1994 | Kambara et al. | 356/344 |
| 5,366,608 | 11/1994 | Kambara | 204/603 |
| 5,529,679 | 6/1996 | Takahashi et al. | 204/603 |
| 5,565,322 | 10/1996 | Heller | 435/6 |
| 5,730,850 | 3/1998 | Kambara et al. | 204/603 |
| 5,770,369 | 6/1998 | Meade et al. | 435/6 |

FOREIGN PATENT DOCUMENTS

| | | |
|---|---|---|
| 2-269936 | 11/1990 | Japan . |
| 3-293557 | 12/1991 | Japan . |
| 5-60698 | 3/1993 | Japan . |
| 5-72177 | 3/1993 | Japan . |
| 5-296978 | 11/1993 | Japan . |
| 6-138037 | 5/1994 | Japan . |
| 95/28636 | 10/1995 | WIPO . |

METHOD AND APPARATUS FOR ELECTROPHORESIS SEPARATION AND DETECTION

BACKGROUND OF THE INVENTION

1. Field of the Invention

The present invention relates to a method for electrophoresis separation and detection of substances in living bodies, such as DNA, and an apparatus for the electrophoresis separation and detection. It relates to, in particular, a method for electrophoresis analysis in which a plurality of fluorophore-labeled samples are analyzed in one and the same lane, and an apparatus for the electrophoresis analysis.

2. Description of the Related Art

With the advance of Human Genome Program and DNA diagnosis, there is a growing demand for rapid determination of the base sequences of two or more kinds of DNA's and examination using various DNA probes. In the determination of the base sequences of DNA's and the measurement for DNA diagnosis, there has come to be used a technique comprising separating fluorophore-labeled DNA's (the same applies also to substances other than DNA, such as sugars and peptides) by gel electrophoresis and measuring the migrating DNA's in real time. For increasing the number of samples which can be measured at the same time, there are, for example, the following requirements: (1) the number of lanes are increased, (2) the electrophoretic migration rate is increased to increase the throughput, and (3) more kinds of labeling fluorophores (a larger number of colors, i.e. fluorescence emission wavelengths) are used.

For assuring a large number of lanes, capillary array electrophoresis apparatus comprising a large number of capillaries with an inner diameter of about 1 mm put side by side have been developed as a substitute for conventional slab gels (JP-A-05-072177, U.S. Pat. No. 5,277,780 and U.S. Pat. No. 5,366,608). Capillary array electrophoresis method is suitable for satisfying the above-mentioned requirements (1) and (2).

On the other hand, in a method comprising labeling two or more kinds of DNA's with many kinds of fluorophores, four kinds of fluorophores are widely used in relation to DNA sequencers. As an exciting light, there are used Ar ion laser (488 nm or 515 nm), YAG laser (532 nm), etc. As the fluorophores, there are often used, for example, FAM (emission wavelength: about 520 nm), JOE (emission wavelength: about 549 nm), TAMRA (emission wavelength: about 575 nm) and ROX (emission wavelength: about 600 nm) which are available from the ABD division of The Perkin-Elmer Corporation, and there are also used FITC (emission wavelength: about 520 nm), Sulforhodamine 101 (emission wavelength: about 615 nm), Cy5 (emission wavelength: about 670 nm), etc. As a means for spectroscopic detection of fluorescences emitted by these fluorophores, there are, for example, time-sharing measurement with a rotating filter, use of an image splitting or dividing prism (JP-A-02-269936 and U.S. Pat. No. 5,062,942), application of wavelength dispersion by means of a prism (JP-A-01-116441 and U.S. Pat. No. 4,832,815) or a grating.

For detecting fluorescences emitted by fluorophores while distinguishing them from one another, it is necessary that the maximum emission wavelengths of the fluorophores should be different from one another by about 30 nm or more. The wavelength region in which the fluorescences are observed is 500 nm to 700 nm, so that only 7 to 8 kinds of fluorophores having different emission wavelengths can be used. Moreover, the number of kinds of fluorophores efficiently excitable by exciting light having one wavelength is 2 or 3. When more kinds of fluorophores are used, two or more kinds of lasers having different wavelengths should be used for exciting the fluorophores. In this case, since the exciting light should be prevented from being received by a photodetector, fluorophores having a maximum emission wavelength near the wavelength of the exciting light are not usable. Therefore, the number of kinds of practically usable fluorophores is limited to about 6.

Kambara and Nagai among the present inventors made the following attempt: two or more kinds of exciting lights having different wavelengths are casted on different places of a gel electrophoresis plate at a definite distance from one another, and the thus obtained fluorescence images are projected on different positions of a photodetector, whereby a plurality of samples are measured at the same time (JP-A-03-293557 and U.S. Pat. No. 5,307,148). However, when too many kinds of fluorophores are used in this method, the detection of fluorescences emitted by all the fluorophores becomes difficult. Therefore, the number of kinds of fluorophores used in this method is limited to 5 or 6. There has recently been proposed a method in which fluorescence is efficiently excited by utilizing excitation energy transfer between two kinds of the fluorophores (JP-A-05-60698 and Anal. Biochem. 231, 131–140 (1995). In addition, as to the efficiency of the energy transfer between the two kinds of the fluorophores as an energy donor and an energy acceptor, respectively, the equation set up by Th. Foerster is known (Annalen der Physik, 6. Folge. Band. 2. (1948) pp. 55–75). According to this reference, the energy transfer rate is inversely proportional to the sixth power of the distance between the energy donor and the energy acceptor and is proportional to the degree of overlapping of an emission spectrum of the energy donor with an absorption spectrum of the energy acceptor. The energy transfer rate is affected also by orientation between the energy donor and the energy acceptor.

L. Stryer and P. H. Haugland have reported experimental investigation on the dependence of the energy transfer on the distance between the energy donor and the energy acceptor (Proc. Natl. Acad. Sci. USA 58 (1967) pp. 719–726). They have revealed good conformity of the distance dependence of the energy transfer with the equation of Foerster by varying the distance between the energy donor and the energy acceptor which are located at the ends of a polypeptide oligomer, by varying the number of the peptides. They obtained energy transfer efficiency values of 100% and 16% at distances between the energy donor and the energy acceptor of 1.2 nm and 4.6 nm, respectively.

SUMMARY OF THE INVENTION

In the field of analysis, in particular, DNA diagnosis and DNA analysis, it is advantageous for labor saving and cost reduction that as many different samples as possible can be analyzed at the same time. In the prior art, it is preferable to use as many kinds of fluorophores as possible as tags, but as explained above, there is a problem in that the number of distinguishable samples is dependent on the number of kinds of usable fluorophores and hence is limited to 6 to 8.

An object of the present invention is to solve this problem and provide a method for electrophoresis separation and detection in which 10 to 20 kinds of samples are individually labeled and then analyzed in one and the same lane at the same time, and an apparatus for the electrophoresis separation and detection.

In the present invention, each label is composed of a combination of a label for excitation and a tag for emission and fluorescence is emitted in a wavelength region distant from the wavelength of exciting light by utilizing energy transfer between the label for excitation and the tag for emission. Furthermore, the kind of the label for excitation is varied and lasers having different wavelengths are used as exciting lights, depending on the kind of the label for excitation, whereby irradiation with the exciting lights is carried out so that the exciting lights can be distinguished with respect to position and time.

The method for electrophoresis separation and detection of the present invention is explained below in further detail. It is an electrophoresis separation and detection method for separating and detecting fluorophore-labeled samples by electrophoresing them in one or more electrophoresis lanes, which comprises a labeling step in which samples are labeled with two or more kinds of fluorophore labels, respectively; an electrophoresis separation step in which the fluorophore-labeled samples are separated by electrophoresis; and a detection step in which the samples separated by electrophoresis are detected by irradiating the fluorophore-labeled samples with two or more kinds of exciting lights having different wavelengths. This method has the following characteristics: each fluorophore label is composed of a substance for excitation which is excited by the exciting light and a substance for emission which emits light owing to energy transfer from the substance for excitation; two or more kinds of substances are used as each of the substance for excitation and the substance for emission; and the two or more kinds of the fluorophore labels are distinguished from one another on the basis of the difference of combination of the two or more kinds of the substances to detect the samples.

As one embodiment, the above-mentioned electrophoresis separation and detection method also has the following characteristics: in a step of casting the two or more kinds of the exciting lights having different wavelengths on the electrophoresis lane at different irradiation positions or times and the detection step, fluorescences emitted by the fluorophore labels, respectively, owing to the irradiation with the exciting lights are detected with wavelength separation, and the wavelengths of the exciting lights are distinguished from those of the fluorescences subjected to the wavelength separation, whereby the fluorophore labels are distinguished to detect the samples; in the detection step, the samples are detected in a solution medium in which the electrophoretic migration rates of the samples are substantially constant; the samples are detected by distinguishing the fluorophore labels by combinations of the wavelengths of the exciting lights and channels for receiving the fluorescences; and the fluorophore-labeled samples are separated by electrophoresis in one and the same electrophoresis lane.

The apparatus for electrophoresis separation and detection of the present invention is an electrophoresis separation and detection apparatus for separating and detecting fluorophore-labeled samples by electrophoresis, which comprises a plurality of electrophoresis lanes for electrophoresis separation of the samples labeled with two or more kinds of fluorophore labels, respectively; light sources which cast two or more kinds of exciting lights having different wavelengths on a plurality of positions, respectively, in all the electrophoresis lanes or on the extensions of all the electrophoresis lanes substantially at the same time; and a detecting means which detects the samples separated by electrophoresis, at the positions on which the exciting lights are casted. This apparatus has the following characteristics: each fluorophore label is composed of a substance for excitation which is excited by the exciting light and a substance for emission which emits light owing to energy transfer from the substance for excitation; two or more kinds of substances are used as each of the substance for excitation and the substance for emission; and the detecting means detects the samples by distinguishing the two or more kinds of the fluorophore labels from one another on the basis of the difference of combination of the two or more kinds of the substances.

As one embodiment, the above-mentioned electrophoresis separation and detection apparatus also has the following characteristics: the irradiating means casts the two or more kinds of the exciting lights having different wavelengths on the electrophoresis lanes at different irradiation positions or times; the detecting means detects fluorescences emitted by the fluorophore labels owing to the irradiation with the exciting lights with wavelength separation, distinguishes the wavelengths of the exciting lights from those of the fluorescences subjected to the wavelength separation, and distinguishes the fluorophore labels to detect the samples; the detecting means detects the samples in a solution medium in which the electrophoretic migration rates of the samples are substantially constant; the detecting means detects the samples by distinguishing the fluorophore labels by combinations of the wavelengths of the exciting lights and channels for receiving the fluorescences; and the fluorophore-labeled samples are separated by electrophoresis in the above-mentioned electrophoresis lane which is one and the same.

In the present invention, on the basis of the results obtained by Von Th. Foerster (Annalen der Physik, 6. Folge. Band. 2. (1948) pp. 55–75) and L. Stryer and P. H. Haugland (Proc. Natl. Acad. Sci. USA 58 (1967) pp. 719–726)), the following can be speculated: when the distance between two fluorophores labeling a DNA fragment as an energy donor and an energy acceptor, respectively, is several nanometers or less and the degree of overlapping of an emission spectrum of the energy donor with an absorption spectrum of the energy acceptor is high, energy transfer takes place between the energy donor and the energy acceptor and moreover the efficiency of the energy transfer can be expected to be 100% or near 100%. That is, when the fluorophore as energy donor is excited, fluorescence emission by the fluorophore as energy acceptor can be efficiently observed. In addition, as compared with the case of labeling only with the fluorophore used as energy donor, the emission wavelength is shifted to the longer wavelength side, so that the difference between the wavelength of exciting light and that of emitted light is increased. Therefore, the measurement of emitted fluorescence is hardly affected by, for example, scattering by the exciting light and hence can be carried out with high sensitivity.

When light emission caused by energy transfer is utilized in the case of choosing two or more kinds of luminous substances excitable at the same wavelength, there can be employed, for example, combinations of one and the same energy donor and two or more kinds of acceptors capable of efficiently receiving transferred energy, or combinations of two more kinds of fluorophores efficiently excitable at the same wavelength or different wavelengths and acceptors capable of efficiently receiving transferred energy from the respective fluorophores. Thus, the fluorophores whose fluorescences are finally detected can be efficiently excited, namely, efficiently detectable fluorophores can be chosen in a wider range. Therefore, the number of kinds of distinguishable labeled DNA's is determined by the number of combinations of labels for excitation used as energy donors and tags for emission used as energy acceptors.

Accordingly, fluorophores having different optimum excitation wavelengths and emission wavelengths are excited by lasers having different wavelengths, and there are prepared, for example, 4 kinds of fluorophores as tags for emission, and a photo-detecting system having 4 light-receiving channels corresponding to the 4 emission wavelengths, respectively, of these fluorophores. Using two kinds of exciting lights having different wavelengths, fluorescences are obtained by exciting the fluorophores for emission by energy transfer from fluorophores efficiently excitable by the exciting lights, respectively. When the two kinds of the exciting lights are distinguished by alternate irradiation with them or by irradiation with them at different irradiation positions, it is possible to know which of the exciting lights is responsible for the light emission. Therefore, the number of kinds of DNA's (sample DNA's) measurable at the same time in distinction from one another is the product of the number of the exciting lights' wavelengths or the number of kinds of labels for excitation and the number of kinds of the tags for emission. Accordingly, a great variety of DNA's can be measured in distinction from one another.

As explained above, according to the present invention, a plurality of samples can be analyzed at the same time by using labels in a number of the product of the number of kinds of energy donor molecules capable of absorbing light and the number of kinds of energy acceptor molecules capable of emitting fluorescence by receiving energy from the energy donor molecules. Even if there cannot be employed a large number of distinguishable wavelength bands in a light-receiving system, a plurality of samples can be measured at the same time in distinction from one another by using a large number of different kinds of labels by varying the kinds of energy donor molecules. Thus, the present invention contributes to various analysis fields including capacity increase of DNA sequencing, simultaneous analysis of a large variety of sample DNA's, etc.

DESCRIPTION OF THE PREFERRED EMBODIMENTS

The present invention is explained in further detail with the following examples with reference to the drawings. Although DNA's were used as samples in the following examples, other substances (e.g. sugars and proteins) can also be used as samples in the same manner as for the DNA's.

EXAMPLE 1

Figure 1:
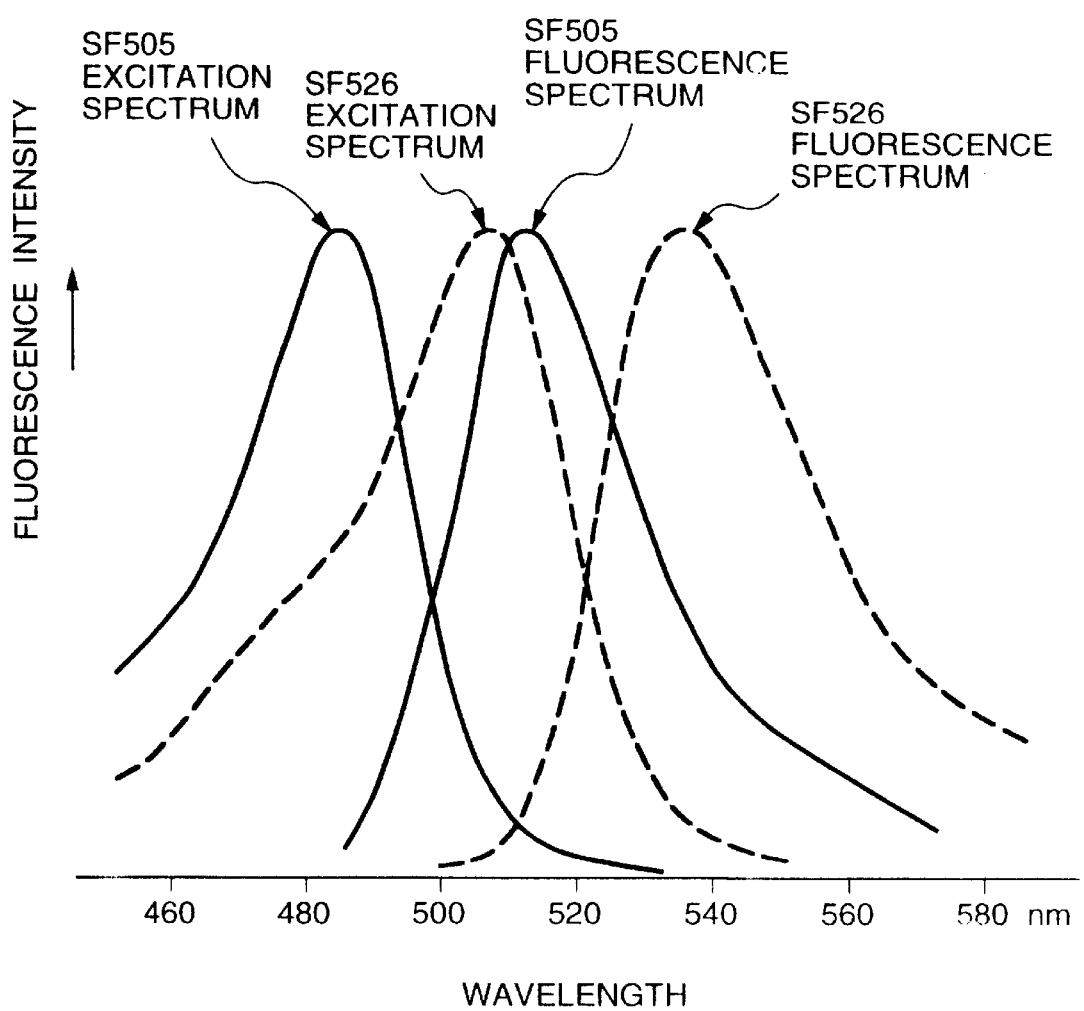
FIG. 1 shows excitation spectra and fluorescence spectra of energy donor molecules (Succinyl Fluoreceins) used in examples of the present invention.

First, there is explained below the preparation of primers (or DNA probes) labeled with one molecule each of a fluorophore for excitation and a fluorophore for emission. As the fluorophore for excitation, there were used two kinds of fluorophores for excitation, SF505 (maximum excitation wavelength 486 nm, maximum emission wavelength 505 nm) and SF526 (maximum excitation wavelength 508 nm, maximum emission wavelength 526 nm) which are isomers of Succinyl Fluorecein (SF). SF505 and SF526 are compounds reported in Science, 238, 336–341 (1987) and have the excitation spectra and fluorescence spectra shown in FIG. 1.

As the fluorophore for emission, there were used 4 kinds of fluorophores for emission, TRITC (maximum excitation wavelength 555 nm, maximum emission wavelength 585 nm), Texas Red (maximum excitation wavelength 594 nm, maximum emission wavelength 615 nm), Cy5 (maximum excitation wavelength 650 nm, maximum emission wavelength 667 nm), and SF505 or SF526. One of the fluorophores for emission may be the same as either of the fluorophores for excitation. The fluorophore for excitation and the fluorophore for emission are bonded to the primer (or the DNA probe) at a distance of 4 bases from each other. There are prepared 8 kinds of primers (or DNA probes) labeled with one molecule each of such a fluorophore for excitation and such a fluorophore for emission.

For the labeling of the primer (or the DNA probe) with the fluorophore for excitation and the fluorophore for emission, the method disclosed in JP-A-61-44353 was employed. This method comprises replacing the phosphoric acid linkage of the polynucleotide at a site of introducing the fluorophore label, by a phosphonic acid linkage having a functional group, and bonding the functional group to the fluorophore to label the polynucleotide with the fluorophore. This method permits introduction of the label into an arbitrary position of the polynucleotide. For labeling the primer (or the DNA probe) with one molecule each of a label for excitation and a tag for emission, the following labeling method was employed. There is carried out a reaction for labeling the primer (or the DNA probe) having phosphonic acid introduced thereinto at a site of introducing the above-mentioned label, with SF505 or SF526 at first.

Figure 2:
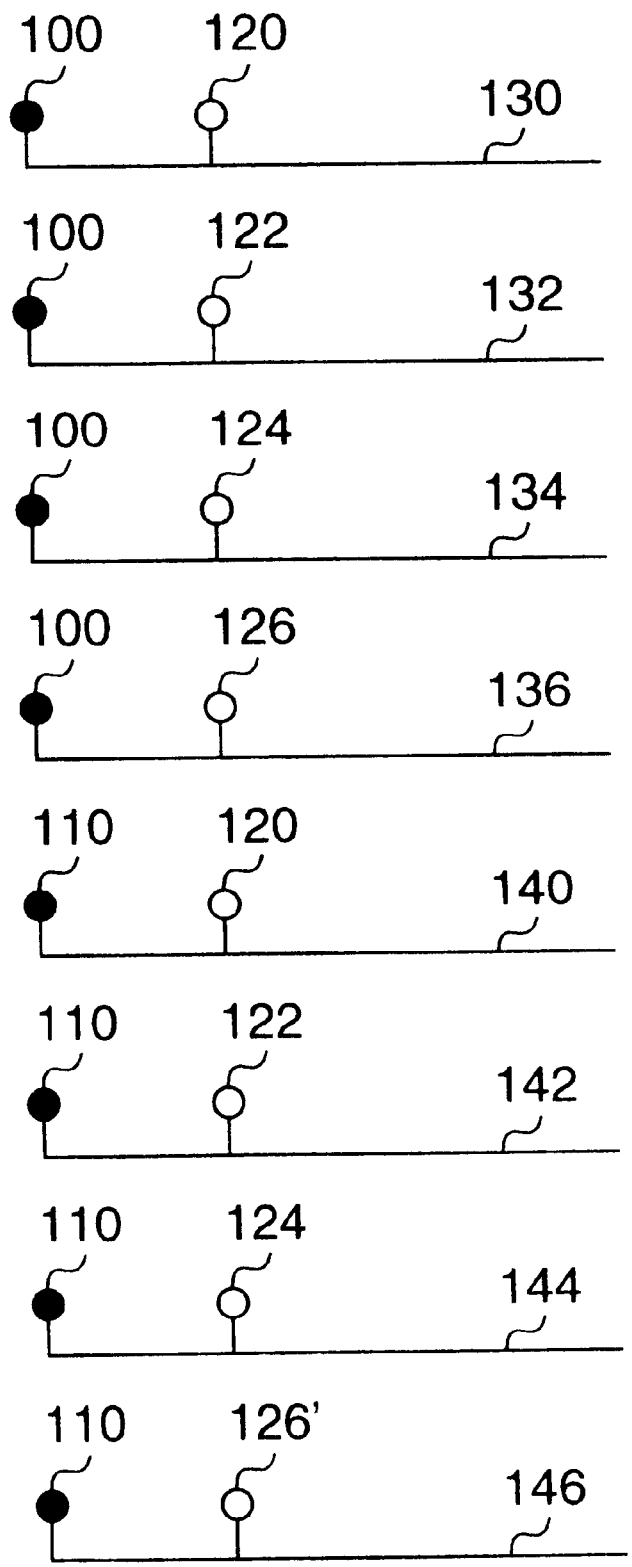
FIG. 2 shows primers used in Example 1 of the present invention.

In this case, the progress of the reaction for introducing SF505 or SF526 into the DNA fragment was estimated by monitoring the reaction product on occasion by liquid chromatography, and comparing absorbance at 260 nm due to DNA with absorbance near 500 nm due to SF505 or SF526. The reaction product is electrophoresed in acrylamide to separate unlabeled primer (or unlabeled DNA probe) from primer (or DNA probe) having one or two molecules of SF505 or SF526 introduced thereinto. A portion of the gel containing a fraction containing the primer (or DNA probe) having one molecule of SF505 or SF526 introduced thereinto is cut out of the gel, and the primer (or DNA probe) contained in the portion is purified. Then, thus purified primer (or DNA probe) labeled with SF505 or SF526 is subjected to a reaction for labeling with a fluorophore for emission. The above reaction process gave the primer (or DNA probe) labeled with one molecule each of the fluorophore for excitation and the fluorophore for emission. FIG. 2 shows primers (or DNA probes) (130, 132, 134, 136, 140, 142, 144 and 146) labeled with a fluorophore for excitation SF505 (100) or SF526 (110) and a fluorophore for emission TRITC (120), Texas Red (122), Cy5 (124), SF505 (126) or SF526 (126').

Although there has been explained above the method for bonding a fluorophore label to the phosphorus atom (P) of the polynucleotide skeleton, it is also possible to attach a label to a base by the method described in Science, 238, 336–341 (1987).

Next, there is explained below the determination of the base sequences of two kinds of different sample DNA's (a and b) by the use of the 8 kinds of the primers (130, 132, 134, 136, 140, 142, 144 and 146) shown in FIG. 2. DNA sequencing reaction is carried out according to the well-known Sanger method. In the case of sample DNA (a), primer 130 is used in a reaction for obtaining DNA fragments terminated by a base A, primer 132 in a reaction for obtaining DNA fragments terminated by a base T, primer 134 in a reaction for obtaining DNA fragments terminated by a base G, and primer 136 in a reaction for obtaining DNA fragments terminated by a base C. In the case of sample DNA (b), primer 140 is used in a reaction for obtaining DNA fragments terminated by a base A, primer 142 in a reaction for obtaining DNA fragments terminated by a base T, primer 144 in a reaction for obtaining DNA fragments terminated by a base G, and primer 146 in a reaction for obtaining DNA fragments terminated by a base C. For each of DNA samples (a) and (b), a specimen for determining the base sequence is obtained by mixing the reaction products obtained for each of the bases A, T, G and C. The specimens for the base sequence determination obtained for DNA samples (a) and (b), respectively, are mixed and supplied to one of the electrophoresis lanes (channels) of an electrophoresis apparatus, followed by electrophoresis separation of DNA fragments in a gel by application of a predetermined voltage. Needless to say, it is also possible to supply the specimens for the base sequence determination obtained for DNA samples (a) and (b) to different electrophoresis lanes (channels), respectively, of the electrophoresis apparatus and separate DNA fragments by electrophoresis.

As the electrophoresis apparatus, there is used an apparatus in which lasers having different wavelengths are casted on different positions, respectively, and fluorescence emitted by the fluorophore labeling each DNA fragment separated by the electrophoresis is detected. Such apparatus have been disclosed in JP-A-3-293557 and U.S. Pat. No. 5,307,148. In the present example, there was used an apparatus in which lasers having different wavelengths are casted on different positions, respectively, in each lane so as to be casted on substantially all the lanes at the same time almost perpendicularly to all the lanes, and fluorescences emitted from two linear light irradiation portions on which the lasers have been casted, respectively, are received by a two-dimensional detector.

As a gel electrophoresis portion where DNA fragments migrate, a slab gel is used in some cases and a capillary gel is used in other cases. In the present example, there was used a capillary array apparatus which has a capillary gel separation portion and permits detection of DNA fragments in a sheath flow. Such capillary array apparatus have been disclosed in JP-A-5-072177, U.S. Pat. No. 5,277,780, U.S. Pat. No. 5,366,608, JP-A-5-296978, JP-A-06-138037, U.S. Pat. No. 5,529,679 and U.S. Pat. No. 5,192,412.

Figure 3:
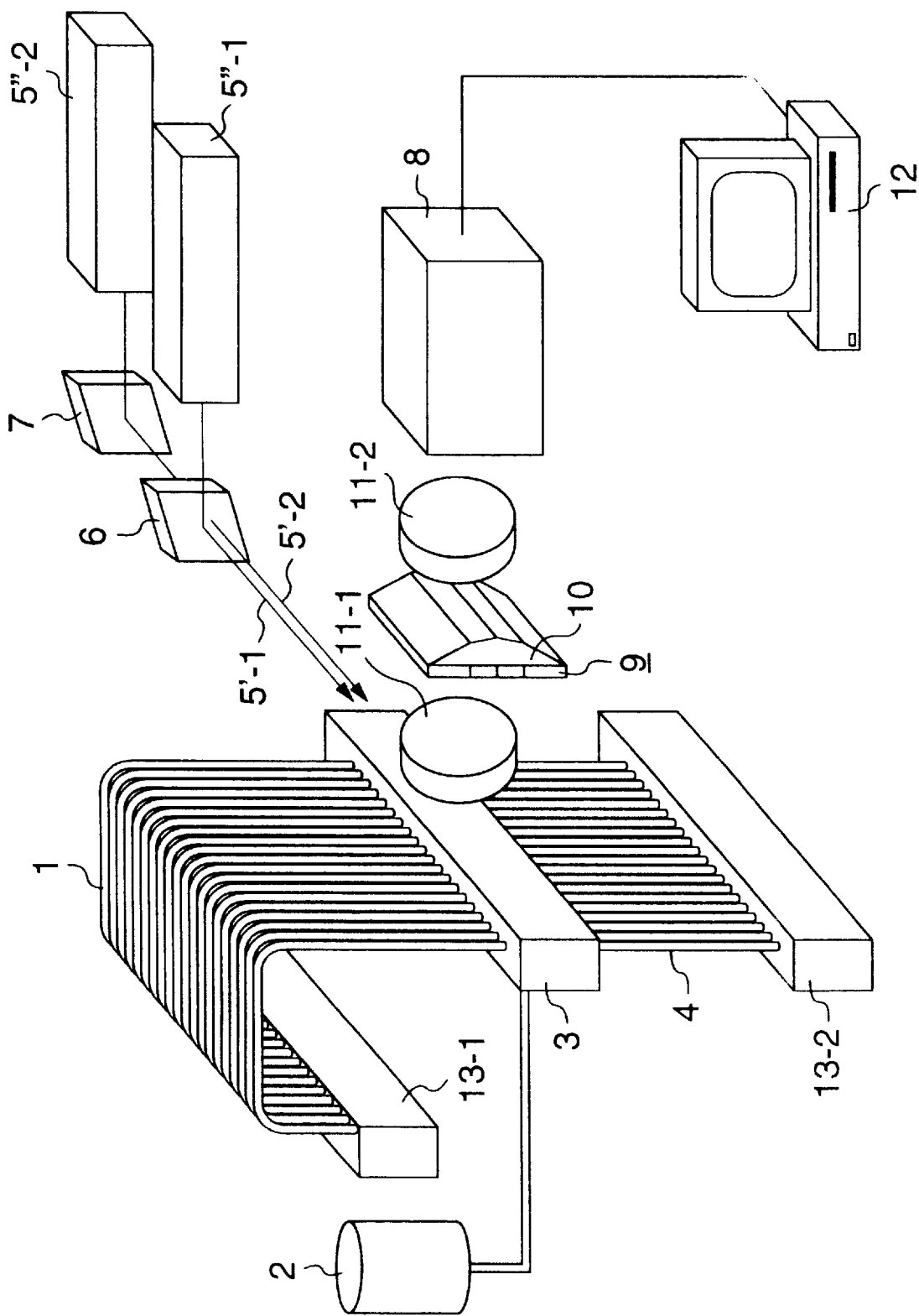
FIG. 3 shows the structure of an electrophoresis apparatus used in Example 1 of the present invention.

The outline of the electrophoresis apparatus used in the present example is shown in FIG. 3. The specimen for the base sequence determination obtained above for DNA sample (a) and that obtained above for DNA sample (b) are mixed and supplied to the migration starting point of one of a plurality of gel capillaries 1, and a voltage is applied by means of electrodes (not shown) in buffer solution tanks 13-1 and 13-2 to separate the DNA fragments by electrophoresis. A plurality of capillaries 4 facing the gel capillaries 1, respectively, with a predetermined gap between each capillary 4 and each capillary 1 are arranged inside a sheath flow cell (light irradiation portion) 3. A sheath solution 2 is poured into the sheath flow cell 3 to form a sheath flow (not shown). DNA fragments separated by the electrophoresis in each gel capillary 1 are eluted from the gel capillary and flow in the above-mentioned gap between the gel capillary 1 and the gel capillary 4 facing thereto, independent of DNA fragments eluted from other gel capillaries.

Ar ion laser sources are used as laser sources 5"-1 and 5"-2. Irradiation with laser 5'-1 (488 nm) and laser 5'-2 (515 nm) inside the sheath flow cell 3 is carried out by means of the laser sources 5"-1 and 5"-2, respectively. The laser 5'-1 (488 nm) and laser 5'-2 (515 nm) are casted on substantially all the lanes at the same time almost perpendicularly to all the lanes through a dichroic mirrors 6 and 7, respectively, at a distance of about 0.5 mm from each other in the direction of electrophoretic migration of DNA fragments. That is, the light irradiation portion inside the sheath flow cell 3 is composed of two linear light irradiation portions, and the lasers 5'-1 and 5'-2 are introduced thereinto along a plane formed by all the lanes, from the transverse direction on the upper stream side and downstream side in the direction of electrophoretic migration to be casted on all the lanes substantially at the same time. In the above-mentioned gap, since fluorescence is emitted from each fluorophore-labeled DNA fragment passing near the intersections of each of the two lasers and the extension of each capillary 1, two groups of point-like fluorescence images aligned in a straight line (two fluorescence line images) are observed.

The fluorescence line images are condensed by a lens 11-1, divided each in four by a color filter [a divided filter composed of a 1-st filter, 2-nd filter, 3-rd filter and 4-th filter (9-1, 9-2, 9-3 and 9-4)] 9 and an image dividing prism 10 (JP-A-02-269936 and U.S. Pat. No. 5,062,942), and then projected on a two-dimensional detector 8 by a lens 11-2 as fluorescence line images subjected to wavelength separation, to be detected. Predetermined processing of the thus detected signals is carried out by a data processing unit 12, whereby information on the base sequences can be obtained. It is also possible to keep a distance between the lasers 5'-1 and 5'-2 of about 0.5 mm in the direction of electrophoretic migration of DNA fragments as described above and cast the lasers 5'-1 and 5'-2 alternately in a time-sharing manner. Alternatively, the lasers 5'-1 and 5'-2 may be casted on the same position alternately in a time-sharing manner instead of keeping a distance between the lasers 5'-1 and 5'-2 of about 0.5 mm in the direction of electrophoretic migration of DNA fragments as described above.

Figure 4:
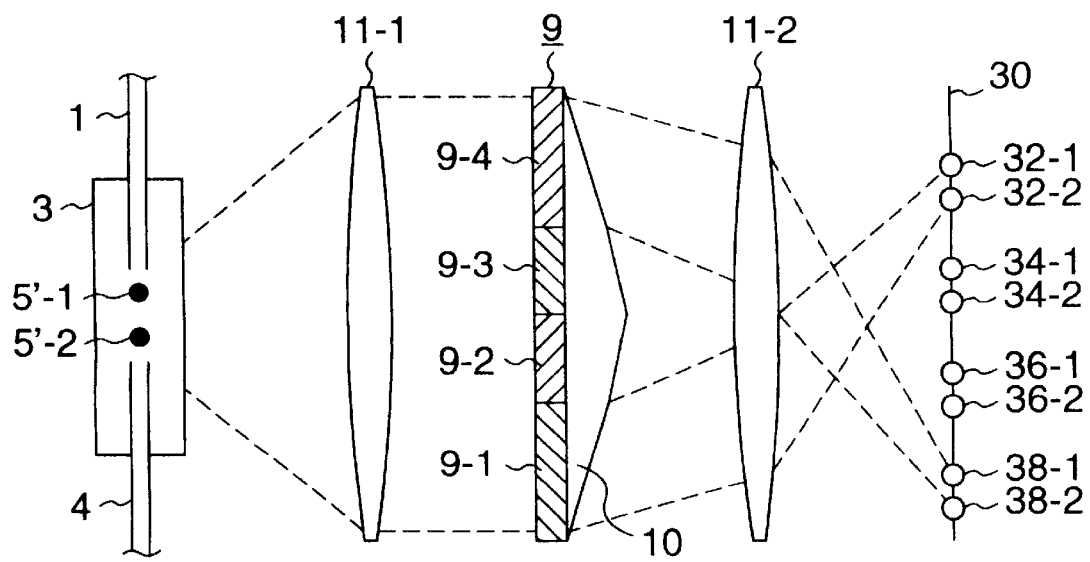
FIG. 4 schematically shows fluorescein images obtained by image division in the electrophoresis apparatus used in Example 1 of the present invention.

As schematically shown in FIG. 4, on the detection plane 30 of the two-dimensional detector 3, there are obtained eight point-like fluorescence images 32-1, 32-2, 34-1, 34-2, 36-1, 36-2, 38-1 and 38-2 by the separation by the divided filter 9 and the image dividing prism 10. The point-like fluorescence images 32-1, 34-1, 36-1 and 38-1 are light images obtained by the detection of fluorescence emitted owing to the irradiation with Ar ion laser (488 nm) and passed through the 1-st filter, 2-nd filter, 3-rd filter and 4-th filter (9-1, 9-2, 9-3 and 9-4), respectively. The point-like fluorescence images 32-2, 34-2, 36-2 and 38-2 are light images obtained by the detection of fluorescence emitted owing to the irradiation with Ar ion laser (515 nm) and passed through the 1-st filter, 2-nd filter, 3-rd filter and 4-th filter (9-1, 9-2, 9-3 and 9-4), respectively. When electrophoresis is carried out by the use of a plurality of electrophoresis lanes by the method described in the present example, a plurality of the schematic patterns shown in FIG. 4 are obtained. FIG. 4 schematically shows fluorescence images obtained by image division by the fluorescence detection system shown in FIG. 3.

When exciting light of 515 nm is casted on the light irradiation portion, only SF526 is excited and each of the four fluorophores for emission [TRITC (120), Texas Red (122), Cy5 (124) and SF526 (126')] emits fluorescence, owing to energy transfer from SF526. The fluorescences having different wavelengths depending on the kind of the fluorophore labeling each DNA fragment are detected in distinction from one another by a color separation and detection system using the image dividing prism. On the other hand, when exciting light of 488 nm is casted on the light irradiation portion, fluorescence emitted from DNA fragments owing to the irradiation with exciting light of 488 nm and fluorescence emitted from DNA fragments owing to the irradiation with exciting light of 515 nm can be detected in distinction from each other because there is a distance of about 0.5 mm between the position of irradiation with exciting light of 488 nm and the position of irradiation with exciting light of 515 nm.

Although exciting light of 488 nm excites both SF505 and SF526, SF526 is inferior in excitation efficiency. The fluorescence intensity attained by the excitation of the above-mentioned 4 fluorophores by energy transfer from SF526 is lower than that attained by the excitation of the above-mentioned 4 fluorophores by energy transfer from SF505. There is a definite relationship between fluorescence intensity values attained by the excitation by energy transfer from SF505 after the excitation of SF505 by exciting light of 488 nm or exciting light of 515 nm, respectively. Since exciting light of 488 nm and exciting light of 515 nm are casted on different positions, respectively, fluorescence can be measured while spatially judging which exciting light induces the emission of the fluorescence.

Therefore, a fluorescence intensity value due to the excitation by energy transfer caused by the excitation of SF505 can be measured alone by measuring fluorescence obtained by the use of exciting light of 515 nm, thereby estimating the proportion of a fluorescence intensity value due to the excitation by energy transfer caused by the excitation of SF526 relative to a fluorescence intensity value attained by the use of exciting light of 488 nm, and subtracting this estimated value from the fluorescence intensity value attained by the use of exciting light of 488 nm. There is explained below an example of method for measuring only the fluorescence intensity value due to the excitation by energy transfer caused by the excitation of SF505.

The ratio of the intensity of exciting light of 488 nm, $I_O(488)$ to the intensity of exciting light of 515 nm, $I_O(515)$ is taken as $\alpha$; the ratio of the efficiency of excitation of SF526 by exciting light of 488 nm, $\beta(SF526/488)$ to the efficiency of excitation of SF526 by exciting light of 515 nm, $\beta(SF526/515)$ is taken as $\gamma$ ($\gamma<1$); and the efficiency of excitation of SF505 by exciting light of 488 nm is taken as $\beta(SF505/488)$. The suffix f used below denotes any of the above-mentioned 4 fluorophores. The ratio of the efficiency of excitation of fluorophore f by energy transfer from SF526 caused by exciting light of 488 nm, $\delta_f(SF526/488)$ to the efficiency of excitation of the fluorophore f by energy transfer from SF526 caused by exciting light of 515 nm, $\delta_f(SF505/488)$ is taken as $\epsilon$; and the efficiency of excitation of the fluorophore f by energy transfer from SF505 caused by exciting light of 488 nm is taken as $\delta_f(SF526/515)$.

$$\alpha = O(488) \div I_O(515) \qquad (1)$$

$$\gamma = \beta(SF526/488) \div \beta(SF526/515) \qquad (2)$$

$$\epsilon = \delta_f(SF526/488) \div \delta_f(SF526/515) \qquad (3)$$

A fluorescence intensity (measured) value due to the excitation by energy transfer from SF526 caused by exciting light of 515 nm, If(SF526/515) is expressed by the equation (4):

$$If(SF526/515) = I_O(515) \times \beta(SF526/515) \times \delta_f(SF526/515) \qquad (4)$$

When a fluorescence intensity value due to the excitation by energy transfer from SF526 caused by exciting light of 488 nm is taken as If(SF526/488) and a fluorescence intensity value due to the excitation by energy transfer from SF505 caused by exciting light of 488 nm is taken as If(SF505/488), a fluorescence intensity (measured) value due to the excitation by energy transfer from SF526 and SF505 caused by exciting light of 488 nm, If((SF526+SF505)/488) is expressed by the equation (5):

$$\begin{aligned} I_f((SF526 + SF505)/488) &= I_f(SF505/488) + \\ & \quad I_f(SF526/488) \\ &= I_0(488) \times \beta(SF505/488) \times \\ & \quad \delta_f(SF505/488) + I_0(488) \times \\ & \quad \beta(SF526/488) \times \delta_f(SF526/488) \end{aligned} \qquad (5)$$

Therefore, the fluorescence intensity value If(SF505/488) can be calculated from the equation (7) shown below, as follows.

$$\begin{aligned} I_f(SF505/488) &= I_f((SF526 + SF505)/488) - \\ & \quad I_0(488) \times \beta(SF526/488) \times \\ & \quad \delta_f(SF526/488) \end{aligned} \qquad (6)$$

In the equation (6), from the equation (2) we get $$\beta(SF526/488) = \gamma \times \beta(SF526/515),$$

and from the equation (3) we get $$\delta_f(SF526/488) = \epsilon \times \delta_f(SF526/515).$$

Thus, we get $$\beta(SF526/488) \times \delta_f(SF526/488) = \gamma \times \epsilon \times \beta(SF526/515) \times \delta_f(SF526/515).$$

Further, from the equation (1) and the equation (4) we get $$\begin{aligned} \beta(SF526/515) \times \delta_f(SF526/515) &= I_f(SF526/515) \div I_0(515) \\ &= I_f(SF526/51) \times \alpha \div I_0(488) \end{aligned}$$

and hence $$\beta(SF526/488) \times \delta_f(SF526/488) = \gamma \times \epsilon \times I_f(SF526/515) \times \alpha \div I_0(488).$$

Therefore, the equation (6) becomes the equation (7):

$$\begin{aligned} I_f(SF505/488) &= I_f((SF526 + SF505)/488) - \\ & \quad \alpha \times \gamma \times \varepsilon \times I_f(SF526/515) \end{aligned} \qquad (7)$$

The fluorescence intensity values due to each exciting light can be measured in the manner described above.

There has been explained above an example of determining the base sequences of two kinds of sample DNA's in one and the same lane by using two kinds of fluorophores for excitation, four kinds of fluorophores for emission, and two kinds of lasers having different wavelengths as exciting lights. In general, by the use of m kinds of fluorophores for excitation, n kinds of fluorophores for emission and k ($k \leq m$) kinds of lasers having different wavelengths as exciting lights, the base sequences of (mxn) kinds of sample DNA's can be determined in one and the same lane. Thus, by preparing two or more kinds of fluorophores for emission and using a detector having such an ability to detect many colors that it can detect fluorescences having different wavelengths emitted by the fluorophores for emission, in distinction from one another, there can be measured sample DNA's in a number determined by the product of the number of exciting light wavelengths or the number of kinds of fluorophores for excitation and the number of kinds of the fluorophores for emission, in optical distinction from one another.

EXAMPLE 2

Although in Example 1, the two kinds of the sample DNA's (8 kinds in terms of samples with different terminal bases for the base sequence determination) were distinguished using the two kinds of the lasers having different wavelengths and the four kinds of the fluorophores for emission, the analysis method described in Example 1 is applicable to measurement using more kinds of lasers and fluorophores. For example, there can be used Ar ion lasers (488 nm and 515 nm) and YAG laser (532 nm); three kinds of fluorophores for excitation, SF505 (maximum excitation wavelength 486 nm, maximum emission wavelength 505 nm), SF526 (maximum excitation wavelength 508 nm, maximum emission wavelength 526 nm) and caeloxy tetramethyl rhodamine (maximum excitation wavelength 540 nm, maximum emission wavelength 566 nm; hereinafter abbreviated as "CATRH" for the sake of simplicity); and four kinds of fluorophores for emission, tetramethyl rhodamine isothiocyanate (TRITC; maximum excitation wavelength 555 nm, maximum emission wavelength 585 nm), XRITC (maximum excitation wavelength 580 nm, maximum emission wavelength 605 nm), Nile Red (maximum excitation wavelength 551 nm, maximum emission wavelength 636 nm) and Cy5 (maximum excitation wavelength 650 nm, maximum emission wavelength 667 nm). The following primers labeled with one molecule each of a fluorophore for excitation and a fluorophore for emission at a distance of 4 bases from each other are prepared in the same manner as in Example 1:

primer (150, not shown) ; SF505+TRITC,
primer (152, not shown) ; SF505+XRITC,
primer (154, not shown) ; SF505+Nile Red,
primer (156, not shown) ; SF505+Cy5,
primer (160, not shown) ; SF526+TRITC,
primer (162, not shown) ; SF526+XRITC,
primer (164, not shown) ; SF526+Nile Red,
primer (166, not shown) ; SF526+Cy5,
primer (170, not shown) ; CATRH+TRITC,
primer (172, not shown) ; CATRH+XRITC,
primer (174, not shown) ; CATRH+Nile Red, and
primer (176, not shown) ; CATRH+Cy5.

There is explained below an example of determining the base sequences of three different sample DNA's (c), (d) and (e) by the use of the above-mentioned 12 kinds of primers. DNA sequencing reaction is carried out according to the well-known Sanger method. In the case of sample DNA (c), primer 150 is used in a reaction for obtaining DNA fragments terminated by a base A, primer 152 in a reaction for obtaining DNA fragments terminated by a base T, primer 154 in a reaction for obtaining DNA fragments terminated by a base G, and primer 156 in a reaction for obtaining DNA fragments terminated by a base C. In the case of sample DNA (d), primer 160 is used in a reaction for obtaining DNA fragments terminated by a base A, primer 162 in a reaction for obtaining DNA fragments terminated by a base T, primer 164 in a reaction for obtaining DNA fragments terminated by a base G, and primer 166 in a reaction for obtaining DNA fragments terminated by a base C. In the case of sample DNA (e), primer 170 is used in a reaction for obtaining DNA fragments terminated by a base A, primer 172 in a reaction for obtaining DNA fragments terminated by a base T, primer 174 in a reaction for obtaining DNA fragments terminated by a base G, and primer 176 in a reaction for obtaining DNA fragments terminated by a base C. For each of DNA samples (c), (d) and (e), a specimen for determining the base sequence is obtained by mixing the reaction products obtained for each of the bases A, T, G and C. The specimens for the base sequence determination obtained for DNA samples (c), (d) and (e), respectively, are mixed and supplied to one of the electrophoresis lanes (channels) of an electrophoresis apparatus, followed by electrophoresis separation of DNA fragments. Needless to say, it is also possible to supply the specimens for the base sequence determination obtained for DNA samples (c), (d) and (e), respectively, to different electrophoresis lanes (channels), respectively, of the electrophoresis apparatus and separate DNA fragments by electrophoresis.

In the present example, the same capillary array type gel electrophoresis apparatus as in Example 1 was used. The specimens for the base sequence determination obtained above for DNA samples (c), (d) and (e), respectively, (12 kinds in terms of samples with different terminal bases for the base sequence determination) are mixed and supplied to the migration starting point of one of a plurality of gel capillaries 1.

Figure 5A:
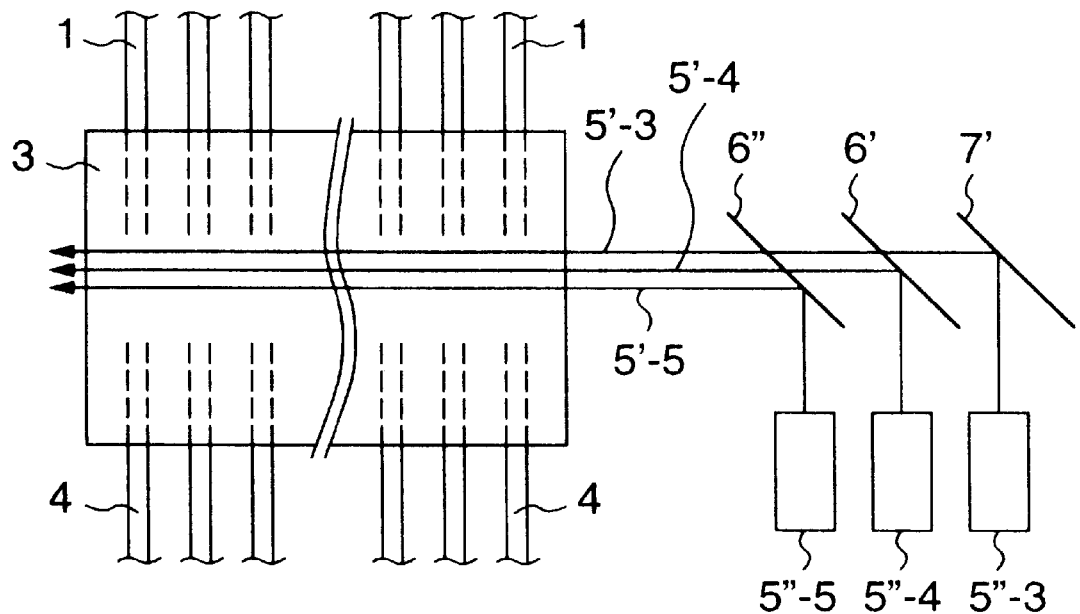
FIG. 5A and FIG. 5B show the mechanisms of irradiation with exciting lights in an electrophoresis apparatus used in Example 2 of the present invention.

As shown in FIG. 5A, in a gap between each gel capillary 1 and each capillary 4, exciting light with a wavelength of 532 nm (5'-3), exciting light with a wavelength of 515 nm (5'-4) and exciting light with a wavelength of 488 nm (5'-5) from a YAG laser source 5"-3, an Ar ion laser source 5"-4 and an Ar ion laser source 5"-5, respectively, are casted on positions inside the sheath flow cell at distances of 0.5 mm, 0.8 mm and 1.1 mm, respectively, from the gel lower end, i.e., the migration end of the gel capillary 1. As shown in FIG. 5A, the laser 5'-3 (532 nm), laser 5'-4 (515 nm) and laser 5'-5 (488 nm) equally spaced 0.3 mm apart in the direction of electrophoretic migration of DNA fragments by a mirror 7' and dichroic mirrors 6 and 6' are casted on substantially all the lanes at the same time almost perpendicularly to all the lanes. A method for fluorescence detection is the same as in Example 1.

DNA fragments separated by the electrophoresis in each gel capillary 1 are eluted from the gel capillary and flow in the above-mentioned gap between the gel capillary 1 and the gel capillary 4 facing thereto, independent of DNA fragments eluted from other gel capillaries. The light irradiation portion inside the sheath flow cell 3 is composed of three linear light irradiation portions, and the lasers 5'-3, 5'-4 and 5'-5 are introduced thereinto along a plane formed by all the lanes, from the transverse direction to be casted on all the lanes substantially at the same time. In the above-mentioned gap, since fluorescence is emitted from each fluorophore-labeled DNA fragment passing near the intersections of each of the three lasers and the extension of each capillary 1, three groups of point-like fluorescence images aligned in a straight line (three fluorescence line images) are observed.

Figure 5B:
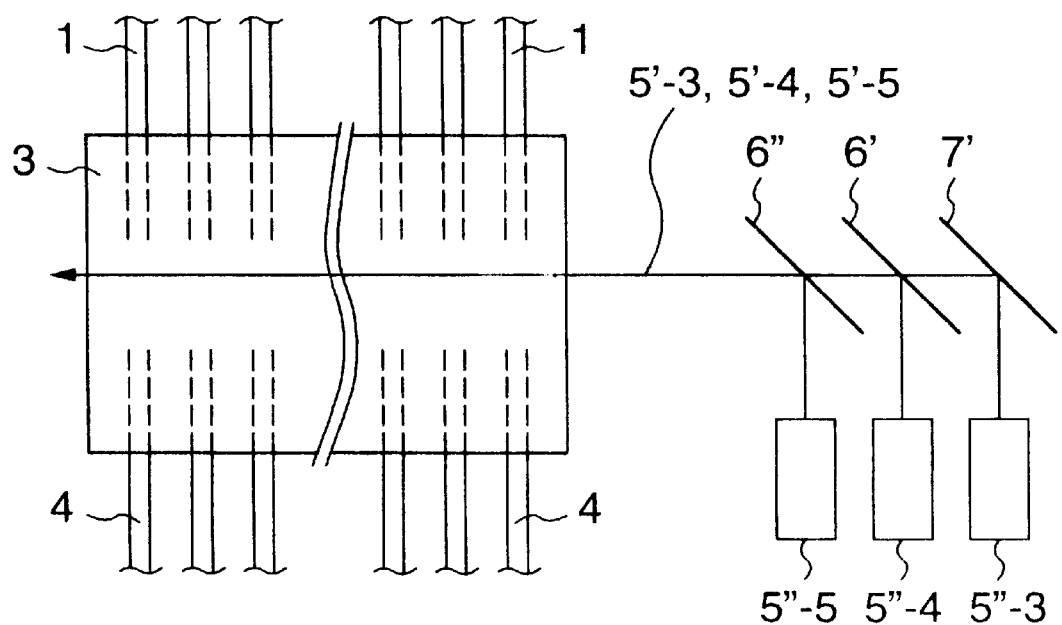

It is also possible to space the lasers 5'-3, 5'-4 and 5'-5 equally about 0.3 mm apart in the direction of electrophoretic migration of DNA fragments as described above, and cast them alternately in a time-sharing manner. Alternatively, as shown in FIG. 5B, the lasers 5'-3, 5'-4 and 5'-5 may be alternately casted on the same position in a time-sharing manner instead of equally spacing the lasers 5'-3, 5'-4 and 5'-5 about 0.3 mm apart in the direction of electrophoretic migration of DNA fragments as described above.

Each of the three groups of point-like fluorescence images (three fluorescence line images) observed on the laser paths are detected while distinguishing fluorescences emitted by the four fluorophores. The detection is carried out using the same color separation and detection system as in Example 1. Although there was used the combination of the image dividing prism, filter and two-dimensional detector explained in Example 1, two or four two-dimensional detectors may be used.

The following is also possible: lasers are casted on lanes (electrophoresis lanes in a slab gel or a capillaries array) in a time-sharing manner by scanning the lasers; which lane is under irradiation is judged from the timing of irradiation by the laser scanning; and fluorescence obtained from the lane under irradiation is received by a one- or two-dimensional detector equipped with a spectroscopic means or a multi-color filter. The wavelength of the lasers scanned may be different for different combinations of a plurality of electrophoresis lanes or for different lanes.

Figure 6:
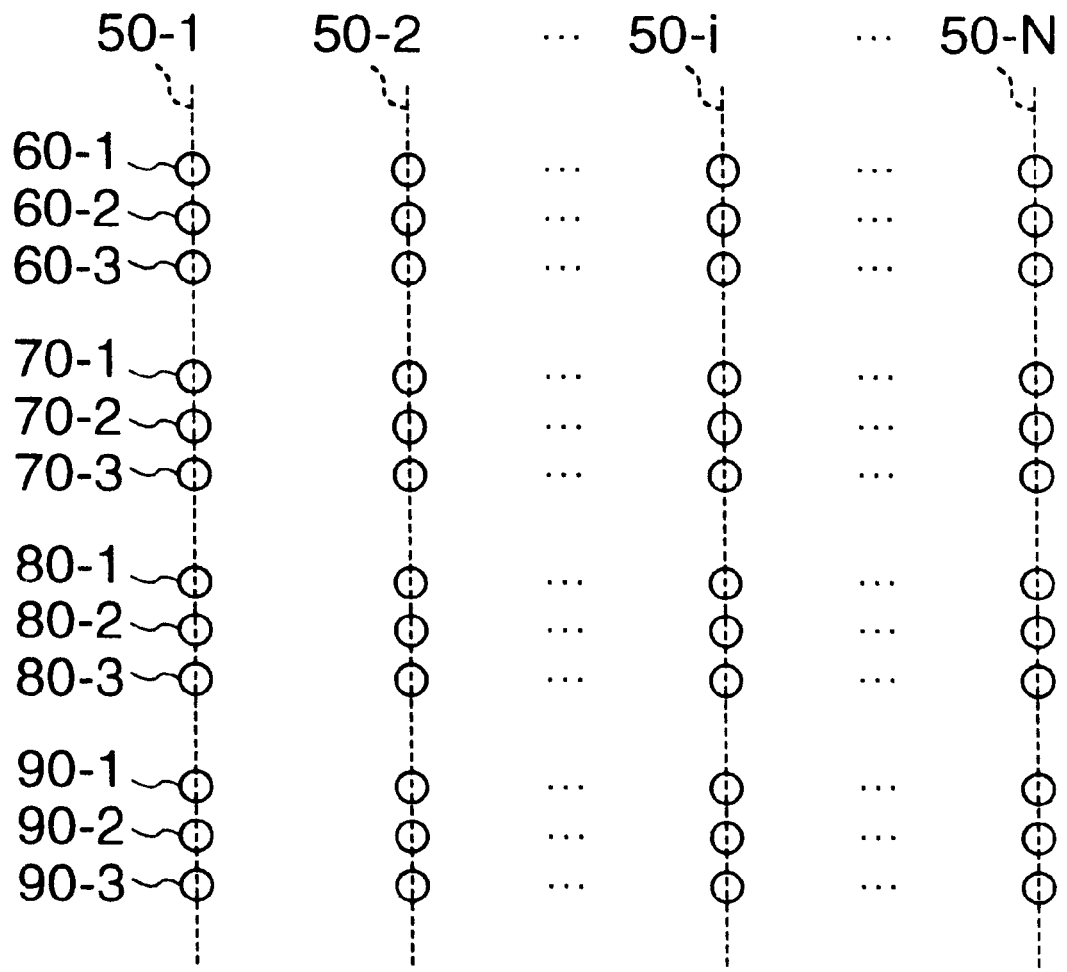
FIG. 6 schematically shows fluorescence images obtained by image division in the electrophoresis apparatus used in Example 2 of the present invention.

The three point-like fluorescence images (fluorescence line images) are divided each in four and projected on the detector as 12 fluorescence line images in total through the filter. FIG. 6 schematically shows the fluorescence images received. There are observed four groups of three fluorescence line images each, in accordance with the number of the exciting light wavelengths. Since the irradiation position is different for the different exciting lights various in wavelength, the same DNA fragment is measured at each irradiation position in some cases. The movement of the DNA fragment between the three positions of exciting light irradiation requires a certain time, and hence the following color separation should be carried out while correcting the migration time of the DNA fragment for a time lag in view of the movement time. As schematically shown in FIG. 6, on the detection plane 30 of the two-dimensional detector 8 shown in FIG. 2, there are obtained 12 point-like fluorescence images in total, 60-1 to 60-3, 70-1 to 70-3, 80-1 to 80-3 and 90-1 to 90-3 which have been separated by the divided filter 9 and the image dividing prism 10.

In the present example, since the DNA fragment samples are migrated in the electrophoresis lane 50-1, the point-like fluorescence images 60-1, 70-1, 80-1 and 90-1 are light images obtained by the detection of fluorescence emitted owing to the irradiation with the laser 5'-3 (532 nm) and passed through the 1-st filter, 2-nd filter, 3-rd filter and 4-th filter (9-1, 9-2, 9-3 and 9-4), respectively; the point-like fluorescence images 60-2, 70-2, 80-2 and 90-2 are light images obtained by the detection of fluorescence emitted owing to the irradiation with the laser 5'-4 (515 nm) and passed through the 1-st filter, 2-nd filter, 3-rd filter and 4-th filter (9-1, 9-2, 9-3 and 9-4), respectively; and the point-like fluorescence images 60-3, 70-3, 80-3 and 90-3 are light images obtained by the detection of fluorescence emitted owing to the irradiation with the laser 5'-5 (488 nm) and passed through the 1-st filter, 2-nd filter, 3-rd filter and 4-th filter (9-1, 9-2, 9-3 and 9-4), respectively. When electrophoresis is carried out by the use of a plurality of electrophoresis lanes 50-2, -----, 50-i, ---, 50-N by the method described in the present example, a plurality of the same patterns as the schematic pattern obtained in the case of using the lane 50-1 are obtained as shown in FIG. 6.

In general, in the electrophoresis of a DNA fragment in a gel, the electrophoretic migration rate varies depending on the length of the DNA fragment, so that the migration time of the DNA fragment is difficult to correct. A method using a sheath flow is advantageous in that the correction is easy because the movement of each DNA fragment between the irradiation positions of the above-mentioned exciting lights depends only on the sheath flow rate but not on the length of the DNA fragment. Between the fluorescence intensity values observed and the amounts of DNA fragments labeled with each dye, there is a relationship represented by the equation (8):

$$I = AC \quad I_j = \Sigma A_{ij} C_j \qquad (8)$$

wherein I is a matrix representing fluorescence intensity values in fluorescence channels ($i=1, 2, ---, j_{max}$) which are detected in a detector; C is a matrix representing the concentrations of the labeled DNA fragments; A is a transformation matrix correlating the matrix I with the matrix C; the elements of matrix $I_j$ ($j=1, 2, ---,$ (the number of fluorophore labels for emission=$j_{max}$)) are the fluorescence intensity values in the fluorescence channels ($i=1, 2, ---, j_{max}$) which are detected in the detector; and $C_j$ is the concentration of each labeled DNA fragment. The elements of matrix $A_{ij}$ are obtained by measuring fluorescence emitted from DNA labeled with each fluorophore for emission of a known concentration owing to excitation by each of three kinds of lasers having different wavelengths. The amounts of the DNA fragments labeled with each fluorophore can be calculated from signals observed in each channel (signals detected with color separation in accordance with the irradiation with each laser), by forming inverse matrix A-1 of the matrix A. In the equation (8), the addition $\Sigma$ is carried out under the condition that $i=1, 2, ---, J_{max}$.

In the above explanation, the positions of laser irradiation are different and the fluorophores for excitation which are effectively excitable by the lasers, respectively, having different wavelengths are distinguished by the difference among the spatial positions of fluorescences emitted from the irradiation positions. It is also possible to distinguish the fluorophores for excitation by casting the lasers alternately with a definite time interval between the casting of the laser having one wavelength and that of the laser having another wavelength. This method is advantageous particularly when DNA fragments migrating in a gel electrophoresis lane are irradiated without a sheath flow. Signals are read in a detector simultaneously with the irradiation with the laser of each wavelength to measure fluorescence, whereby the fluorescence from the laser irradiation position is detected while distinguishing the fluorophores for excitation.

The following detection method can also be employed: the positions of irradiation with two or more kinds of lasers, respectively, are made different by adopting a technique comprising irradiation on the same irradiation line by laser scanning, and fluorescence from each emission position is detected with color separation by means of a detector capable of detecting the irradiation positions.

In the present example, the base sequences were determined by electrophoresing the three kinds of the DNA samples in one and the same electrophoresis lane, though when a plurality of electrophoresis lanes, for example, 100 electrophoresis lanes are used, the base sequences of 300 kinds of sample DNA's can be determined by one run of electrophoresis. In the present example, when the number of positions on which lasers, respectively, are casted is increased from 3 to 4, 5, ---, the base sequences of 4, 5, ---, respectively, kinds of sample DNA's can be determined in one and the same electrophoresis lane. Therefore, when 100 electrophoresis lanes are used, the base sequences of 400, 500, --- kinds of sample DNA's can be determined by one run of electrophoresis.

EXAMPLE 3

Although the determination of the base sequences of sample DNA's has been explained in Examples 1 and 2, a plurality of samples can be examined and analyzed for the polymorphism of fragments obtained by restriction enzyme digestion of DNA (RFLP), at the same time in one and the same electrophoresis lane in the same manner as in the above examples by using the DNA probes shown in FIG. 2. When there are used the various fluorophores used in Example 2 and a plurality of electrophoresis lanes, for example, 100 electrophoresis lanes, 300 kinds of sample DNA's can be examined and analyzed for RFLP by one run of electrophoresis.

EXAMPLE 4

When a sample of double-stranded DNA is amplified by PCR, separated into individual strands and then electrophoresed, the +strand and the –strand are different in electrophoretic migration rate because of their different helical structures. The present invention is applicable also to such a PCR-SSCP (single strand configuration polymorphism) method comprising separating DNA amplified by PCR into individual strands and electrophoresing the +strand and the –strand to detect the configuration polymorphism of each single strand. Using the plurality of the primers explained in Examples 1 or 2, a normal sample of double-stranded DNA having a normal base sequence and a plurality of general samples of double-stranded DNA are amplified by PCR, and each amplified sample double-stranded DNA is separated to individual strands, after which the +strands and –strands thus obtained from the samples are mixed and then electrophoresed in one and the same electrophoresis lane.

For example, when the plurality of the primers explained in Examples 1 are used, 8 samples in total (one kind of normal sample and 7 kinds of general samples) are mixed. When the plurality of the primers explained in Examples 2 are used, 12 samples in total (one kind of normal sample and 11 kinds of general samples) are mixed. The resulting mixture in the former or latter case is electrophoresed by the use of the exciting lights explained in Example 1 or 2, respectively, to obtain electrophoretic patterns. By comparing the electrophoretic patterns obtained for the normal sample and each general sample, respectively, the mutation of double-stranded DNA can be efficiently detected. Thus, many kinds (for example, 7 kinds or 11 kinds) of general samples can be compared always with one normal sample as standard as described above, so that the mutation of double-stranded DNA can be efficiently and accurately detected. When electrophoresis lanes in a number of n are used, very many kinds (for example, 7×n kinds or 11×n kinds) of general samples can be examined by one run of electrophoresis, whereby gene mutation can be detected.

EXAMPLE 5

The present invention is applicable also to the analysis of sugars, proteins, etc. In carrying out the quantitative analysis of the reactions of sugars, proteins or the like, the sugars, proteins or the like which participate in the reactions are labeled with such various fluorophores as are explained in Examples 1 or 2, and the reaction products are electrophoresed and the fluorophore labels are detected by the use of two or more kinds of lasers having different wavelengths by the same method as in Example 1 or 2, whereby the quantitative analysis of the sugars, proteins or the like can be efficiently carried out.

As can be seen from the examples explained above, according to the present invention, 12 kinds of general samples can be analyzed in one and the same electrophoresis lane, for example, in Example 2. Therefore, when 100 electrophoresis lanes are used, 1,200 kinds of general samples can be analyzed by one run of electrophoresis. Furthermore, when the number of positions on which lasers, respectively, are casted as exciting lights is increased from 3 to 4, 5, ---, 16, 20, --- kinds, respectively, of general samples can be analyzed in one and the same electrophoresis lane.

Therefore, when 100 electrophoresis lanes are used, 1,600, 2,000, --- kinds of general samples can be analyzed by one run of electrophoresis. In the case of base sequence determination, the base sequences of 400, 500, --- kinds of sample DNA's can be determined by one run of electrophoresis.

The present inventive electrophoresis apparatus for analyzing a plurality of fluorophore-labeled samples in one and the same lane is summarized below with reference to FIG. 3. Using two or more kinds of fluorophores as energy donors, energy acceptor molecules are excited by energy transfer from the energy donors to emit fluorescence. Specimens for determining the base sequences of a plurality of DNA samples are mixed and supplied to the migration starting point of one of gel capillaries 1. Capillaries 4 facing the gel capillaries 1, respectively, with a predetermined gap between each capillary 4 and each capillary 1 are arranged inside a sheath flow cell 3 into which a sheath solution 2 is poured, and a sheath flow is formed inside the sheath flow cell 3. Irradiation with lasers 5'-1 and 5'-2 spaced 0.5 mm apart is carried out inside the sheath flow cell 3. The fluorescence line images emitted from fluorophore-labeled DNA fragments in each gap are condensed, divided each in four by a divided filter composed of 1-st to 4-th filters (9-1 to 9-4) and an image dividing prism 10, and then projected on a two-dimensional detector 8 to be detected. The thus detected signals are subjected to predetermined processing to obtain information on the base sequences finally. The electrophoresis apparatus permits easy distinction among substances in living bodies, such as many kinds of DNA's.

This application is based on Japanese Patent Application No. 08-168977 filed Jun. 28, 1996, the content of which is in its entirety incorporated hereinto by reference.

What is claimed is:

1. An electrophoresis separation and detection method for separating and detecting samples labeled with fluorophore labels, respectively, by electrophoresis, comprising the steps of:

separating the samples labeled with the fluorophore labels, respectively, by electrophoresis in at least one electrophoresis lane; and detecting the samples separated by the electrophoresis by irradiating the samples labeled with the fluorophore labels, respectively, with at least two kinds of exciting lights having different wavelengths;

wherein each of the fluorophore labels is composed of a substance for excitation which is excited by the exciting light and a substance for emission which emits light owing to energy transfer from the substance for excitation;

wherein at least two kinds of substances are used as each of the substance for excitation and the substance for emission; and wherein the at least two kinds of the fluorophore labels are distinguished from one another based on a difference of a combination of the at least two kinds of the substances used as the substance for excitation and those used as the substance for emission, to detect the samples.

2. An electrophoresis separation and detection method according to claim 1, wherein in the detecting step, at least two kinds of exciting lights having different wavelengths are cast on the at least one electrophoresis lane at different positions or times, fluorescences emitted by the fluorophore labels, respectively, owing to the irradiation with the exciting lights are detected with wavelength separation, and the wavelengths of the exciting lights are distinguished from those of the fluorescences subjected to the wavelength separation, whereby the fluorophore labels are distinguished to detect the samples.

3. An electrophoresis separation and detection method according to claim 2, wherein in the detecting step, the samples are detected in a solution medium in which the migration rates of the samples are substantially constant.

4. An electrophoresis separation and detection method according to claim 2, wherein the samples are detected by distinguishing the fluorophore labels by combinations of the wavelengths of the exciting lights and channels for receiving the fluorescences.

5. An electrophoresis separation and detection method according to claim 2, wherein the samples labeled with the fluorophores, respectively, are separated by electrophoresis in each one of the at least electrophoresis lane.

6. An electrophoresis separation and detection system for separating and detecting samples labeled with fluorophore labels, respectively, by electrophoresis, comprising:

a plurality of electrophoresis lanes for electrophoresis separation containing samples labeled with at least two kinds of the fluorophore labels, respectively;

irradiating means which casts at least two kinds of exciting lights having different wavelengths on a plurality of positions, respectively, in all of the electrophoresis lanes or on extensions of all of the electrophoresis lanes substantially at the same time; and detecting means which detects the samples separated by the electrophoresis, at the positions on which the exciting lights are cast;

wherein each of the fluorophore labels is composed of a substance for excitation which is excited by the exciting light and a substance for emission which emits light owing to energy transfer from the substance for excitation;

wherein at least two kinds of substances are used as each of the substance for excitation and the substance for emission; and wherein the detecting means detects the samples by distinguishing the at least two kinds of the fluorophore labels from one another based on a difference of a combination of the at least two kinds of the substances used as the substance for excitation and those used as the substance for emission.

7. An electrophoresis separation and detection apparatus according to claim 6, wherein the irradiating means casts the at least two kinds of the exciting lights having different wavelengths on the electrophoresis lanes at different positions or times; and wherein the detecting means detects fluorescences emitted by the fluorophore labels, respectively, owing to the irradiation with the exciting lights with wavelength separation, distinguishes the wavelengths of the exciting lights from those of the fluorescences subjected to the wavelength separation, and distinguishes the fluorophore labels to detect the samples.

8. An electrophoresis separation and detection apparatus according to claim 7, wherein the detecting means detects the samples in a solution medium in which the migration rates of the samples are substantially constant.

9. An electrophoresis separation and detection apparatus according to claim 7, wherein the detecting means detects the samples by distinguishing the fluorophore labels by combinations of the wavelengths of the exciting lights and channels for receiving the fluorescences.

10. An electrophoresis separation and detection apparatus according to claim 7, wherein the samples labeled with the fluorophore labels, respectively, are separated by electrophoresis in each one of the electrophoresis lanes.

11. An electrophoresis separation and detection system for separating and detecting samples labeled with fluorophore labels, respectively, by electrophoresis, comprising:

a plurality of electrophoresis lanes for electrophoresis separation containing samples labeled with at least two kinds of the fluorophore labels, respectively;

light sources which cast at least two kinds of exciting lights having different wavelengths on a plurality of positions, respectively, in all of the electrophoresis lanes or on the extensions of all of the electrophoresis lanes substantially at the same time; and photo-detecting means which detects the samples separated by the electrophoresis, at the positions on which the exciting lights are cast;

wherein each of the fluorophore labels is composed of a substance for excitation which is excited by the exciting light and a substance for emission which emits light owing to energy transfer from the substance for excitation;

wherein at least two kinds of substances are used as each of the substance for excitation and the substance for emission; and wherein the photo-detecting means detects the samples by distinguishing the at least two kinds of the fluorophore labels from one another based on a difference of a combination of the at least two kinds of the substances used as the substance for excitation and those used as the substance for emission.

12. An electrophoresis separation and detection apparatus according to claim 11, wherein the light sources cast the at least two kinds of the exciting lights having different wavelengths on the electrophoresis lanes at different positions or times; and wherein the photo-detecting means detects fluorescences emitted by the fluorophore labels, respectively, owing to the irradiation with the exciting lights with wavelength separation, distinguishes the wavelengths of the exciting lights from those of the fluorescences subjected to the wavelength separation, and distinguishes the fluorophore labels to detect the samples.

13. An electrophoresis separation and detection apparatus according to claim 12, wherein the photo-detecting means detects the samples in a solution medium in which the migration rates of the samples are substantially constant.

14. An electrophoresis separation and detection apparatus according to claim 12, wherein the photo-detecting means detects the samples by distinguishing the fluorophore labels by combinations of the wavelengths of the exciting lights and channels for receiving the fluorescences.

15. An electrophoresis separation and detection apparatus according to claim 12, wherein the samples labeled with the fluorophore labels, respectively, are separated by electrophoresis in each one of the electrophoresis lanes.

16. An electrophoresis method comprising the steps of:
   (1) separating a plurality of mixtures of different samples in a plurality of electrophoresis lanes disposed in parallel in a plane,
   each of the mixtures being separated in a different one of the electrophoresis lanes,
   each of the samples including a plurality of different sample fragments,
   each of the sample fragments being labeled with a first fluorophore constituting an energy donor, and a second fluorophore constituting an energy acceptor,
   the first fluorophore being the same for all of the different sample fragments of any particular one of the different samples, and being different for each of the different samples,
   a combination of the first fluorophore and the second fluorophore being different for each of the different sample fragments of each of the different samples,
   the sample fragments migrating through the electrophoresis lanes into a solution medium,
   the sample fragments migrating through the solution medium along paths respectively extending from the electrophoresis lanes at respective migration rates which are substantially constant and do not depend on respective lengths of the sample fragments;
   (2) irradiating the sample fragments migrating through the solution medium with a plurality of exciting lights simultaneously at a plurality of positions on each of the paths extending from the electrophoresis lanes from a direction perpendicular to the electrophoresis lanes and parallel to the plane in which the electrophoresis planes are disposed,
   each of the exciting lights having a different wavelength and being irradiated at a different one of the positions,
   the exciting lights exciting the first fluorophore,
   the excited first fluorophore transferring energy to the second fluorophore, causing the second fluorophore to emit fluorescence in the solution medium;
   (3) detecting the fluorescence emitted in the solution medium by the second fluorophore through a plurality of channels; and
   (4) detecting the different sample fragments of the different samples from the detected fluorescence based on combinations of the wavelengths of the exciting lights and the channels.

17. An electrophoresis method according to claim 16, wherein the solution medium is a sheath solution flowing in a sheath flow; and
   wherein the migration rates of the sample fragments in the sheath solution depend on a flow rate of the sheath flow.

18. An electrophoresis method comprising the steps of:
   (1) separating a plurality of mixtures of different samples in a plurality of electrophoresis lanes disposed in parallel in a plane,
   each of the mixtures being separated in a different one of the electrophoresis lanes,
   each of the samples including a plurality of different sample fragments,
   each of the sample fragments being labeled with a first fluorophore constituting an energy donor, and a second fluorophore constituting an energy acceptor,
   the first fluorophore being the same for all of the different sample fragments of any particular one of the different samples, and being different for each of the different samples,
   a combination of the first fluorophore and the second fluorophore being different for each of the different sample fragments of each of the different samples,
   the sample fragments migrating through the electrophoresis lanes into a solution medium,
   the sample fragments migrating through the solution medium along paths respectively extending from the electrophoresis lanes at respective migration rates which are substantially constant and do not depend on respective lengths of the sample fragments;
   (2) irradiating the sample fragments migrating through the solution medium with a plurality of exciting lights time-sequentially at a same position on each of the paths extending from the electrophoresis lanes from a direction perpendicular to the electrophoresis lanes and parallel to the plane in which the electrophoresis planes are disposed,
   each of the exciting lights having a different wavelength and being irradiated at the same position during a different time interval,
   the exciting lights exciting the first fluorophore,
   the excited first fluorophore transferring energy to the second fluorophore, causing the second fluorophore to emit fluorescence in the solution medium;
   (3) detecting the fluorescence emitted in the solution medium by the second fluorophore through a plurality of channels; and
   (4) detecting the different sample fragments of the different samples from the detected fluorescence based on combinations of the wavelengths of the exciting lights and the channels.

19. An electrophoresis method according to claim 18, wherein the solution medium is a sheath solution flowing in a sheath flow; and
   wherein the migration rates of the sample fragments in the sheath solution depend on a flow rate of the sheath flow.

20. An electrophoresis method comprising the steps of:
   (1) separating a plurality of mixtures of different samples in a plurality of electrophoresis lanes disposed in parallel in a plane,
   each of the mixtures being separated in a different one of the electrophoresis lanes,
   each of the samples including a plurality of different sample fragments,
   each of the sample fragments being labeled with a first fluorophore constituting an energy donor, and a second fluorophore constituting an energy acceptor,
   the first fluorophore being the same for all of the different sample fragments of any particular one of the different samples, and being different for each of the different samples, a combination of the first fluorophore and the second fluorophore being different for each of the different sample fragments of each of the different samples, the sample fragments migrating through the electrophoresis lanes;

(2) irradiating the sample fragments migrating through the electrophoresis lanes with a plurality of exciting lights simultaneously at a plurality of positions in each of the electrophoresis lanes from a direction perpendicular to the electrophoresis lanes and parallel to the plane in which the electrophoresis planes are disposed, each of the exciting lights having a different wavelength and being irradiated at a different one of the positions, the exciting lights exciting the first fluorophore, the excited first fluorophore transferring energy to the second fluorophore, causing the second fluorophore to emit fluorescence in the electrophoresis lanes;

(3) detecting the fluorescence emitted in the electrophoresis lanes by the second fluorophore through a plurality of channels; and (4) detecting the different sample fragments of the different samples from the detected fluorescence based on combinations of the wavelengths of the exciting lights and the channels.

21. An electrophoresis apparatus comprising:
 (1) a plurality of electrophoresis lanes, disposed in parallel in a plane and containing a plurality of mixtures of different samples, for electrophoresis separation of each of the mixtures in a different one of the electrophoresis lanes as the samples migrate through the electrophoresis lanes;

wherein each of the samples includes a plurality of different sample fragments;

wherein each of the sample fragments is labeled with a first fluorophore constituting an energy donor, and a second fluorophore constituting an energy acceptor;

wherein the first fluorophore is the same for all of the different sample fragments of any particular one of the different samples, and is different for each of the different samples;

wherein a combination of the first fluorophore and the second fluorophore is different for each of the different sample fragments of each of the different samples;

wherein the electrophoresis apparatus further comprises;
 (2) a vessel which contains a solution medium into which the sample fragments migrate from the electrophoresis lanes and through which the sample fragments migrate along paths respectively extending from the electrophoresis lanes at respective migration rates which are substantially constant and do not depend on respective lengths of the sample fragments; and
 (3) a light irradiating system which irradiates the sample fragments migrating through the solution medium with a plurality of exciting lights each having a different wavelength at a plurality of positions simultaneously on each of the paths extending from the electrophoresis lanes from a direction perpendicular to the electrophoresis lanes and parallel to the plane in which the electrophoresis planes are disposed such that each of the exciting lights is irradiated at a different one of the positions;

wherein the exciting lights excite the first fluorophore;

wherein the excited first fluorophore transfers energy to the second fluorophore, thereby causing the second fluorophore to emit fluorescence in the solution medium; and wherein the electrophoresis apparatus further comprises:
 (4) a fluorescence detecting system which detects the fluorescence emitted in the solution medium by the second fluorophore through a plurality of channels; and
 (5) a sample fragment detecting system which detects the different sample fragments of the different samples from the detected fluorescence based on combinations of the wavelengths of the exciting lights and the channels.

22. An electrophoresis apparatus according to claim 21, wherein the solution medium is a sheath solution;

wherein the electrophoresis apparatus further comprises a sheath flow system which causes the sheath solution to flow in a sheath flow in the vessel; and wherein the migration rates of the sample fragments in the sheath solution depend on a flow rate of the sheath flow.

23. An electrophoresis apparatus comprising:
 (1) a plurality of electrophoresis lanes, disposed in parallel in a plane and containing a plurality of mixtures of different samples, for electrophoresis separation of each of the mixtures in a different one of the electrophoresis lanes as the samples migrate through the electrophoresis lanes;

wherein each of the samples includes a plurality of different sample fragments;

wherein each of the sample fragments is labeled with a first fluorophore constituting an energy donor, and a second fluorophore constituting an energy acceptor;

wherein the first fluorophore is the same for all of the different sample fragments of any particular one of the different samples, and is different for each of the different samples;

wherein a combination of the first fluorophore and the second fluorophore is different for each of the different sample fragments of each of the different samples;

wherein the electrophoresis apparatus further comprises:
 (2) a vessel which contains a solution medium into which the sample fragments migrate from the electrophoresis lanes and through which the sample fragments migrate along paths respectively extending from the electrophoresis lanes at respective migration rates which are substantially constant and do not depend on respective lengths of the sample fragments; and
 (3) a light irradiating system which irradiates the sample fragments migrating through the solution medium with a plurality of exciting lights each having a different wavelength at a same position time-sequentially on each of the paths extending from the electrophoresis lanes from a direction perpendicular to the electrophoresis lanes and parallel to the plane in which the electrophoresis planes are disposed such that each of the exciting lights is irradiated at the same position during a different time interval;

wherein the exciting lights excite the first fluorophore;

wherein the excited first fluorophore transfers energy to the second fluorophore, thereby causing the second fluorophore to emit fluorescence in the solution medium; and wherein the electrophoresis apparatus further comprises:
 (4) a fluorescence detecting system which detects the fluorescence emitted in the solution medium by the second fluorophore through a plurality of channels; and (5) a sample fragment detecting system which detects the different sample fragments of the different samples from the detected fluorescence based on combinations of the wavelengths of the exciting lights and the channels.

24. An electrophoresis apparatus according to claim 23, wherein the solution medium is a sheath solution;

wherein the electrophoresis apparatus further comprises a sheath flow system which causes the sheath solution to flow in a sheath flow in the vessel; and wherein the migration rates of the sample fragments in the sheath solution depend on a flow rate of the sheath flow.

25. An electrophoresis apparatus comprising:

(1) a plurality of electrophoresis lanes, disposed in parallel in a plane and containing a plurality of mixtures of different samples, for electrophoresis separation of each of the mixtures in a different one of the electrophoresis lanes as the samples migrate through the electrophoresis lanes;

wherein each of the samples includes a plurality of different sample fragments;

wherein each of the sample fragments is labeled with a first fluorophore constituting an energy donor, and a second fluorophore constituting an energy acceptor;

wherein the first fluorophore is the same for all of the different sample fragments of any particular one of the different samples, and is different for each of the different samples;

wherein a combination of the first fluorophore and the second fluorophore is different for each of the different sample fragments of each of the different samples;

wherein the electrophoresis apparatus further comprises:

(2) a light irradiating system which irradiates the sample fragments migrating through the electrophoresis lanes with a plurality of exciting lights each having a different wavelength at a plurality of positions simultaneously in each of the electrophoresis lanes from a direction perpendicular to the electrophoresis lanes and parallel to the plane in which the electrophoresis planes are disposed such that each of the exciting lights is irradiated at a different one of the positions;

wherein the exciting lights excite the first fluorophore;

wherein the excited first fluorophore transfers energy to the second fluorophore, thereby causing the second fluorophore to emit fluorescence in the electrophoresis lanes; and wherein the electrophoresis apparatus further comprises:

(3) a fluorescence-detecting system which detects the fluorescence emitted in the electrophoresis lanes by the second fluorophore through a plurality of channels; and (4) a sample fragment detecting system which detects the different sample fragments of the different samples from the detected fluorescence based on combinations of the wavelengths of the exciting lights and the channels.

26. An electrophoresis method comprising the steps of:

(1) separating a mixture of different samples in one electrophoresis lane, each of the samples including a plurality of different sample fragments, each of the sample fragments being labeled with a first fluorophore constituting an energy donor, and a second fluorophore constituting an energy acceptor, the first fluorophore being the same for all of the different sample fragments of any particular one of the different samples, and being different for each of the different samples, a combination of the first fluorophore and the second fluorophore being different for each of the different sample fragments of each of the different samples, the sample fragments migrating through the electrophoresis lane;

(2) irradiating the sample fragments migrating through the electrophoresis lane with a plurality of exciting lights simultaneously at a plurality of positions in the electrophoresis lane, each of the exciting lights having a different wavelength and being irradiated at a different one of the positions, the exciting lights exciting the first fluorophore, the excited first fluorophore transferring energy to the second fluorophore, causing the second fluorophore to emit fluorescence in the electrophoresis lane;

(3) detecting the fluorescence emitted in the electrophoresis lane by the second fluorophore through a plurality of channels; and (4) detecting the different sample fragments of the different samples from the detected fluorescence based on combinations of the wavelengths of the exciting lights and the channels.

27. An electrophoresis apparatus comprising:

(1) one electrophoresis lane, containing a mixture of different samples, for electrophoresis separation of the mixture as the samples migrate through the electrophoresis lane;

wherein each of the samples includes a plurality of different sample fragments;

wherein each of the sample fragments is labeled with a first fluorophore constituting an energy donor, and a second fluorophore constituting an energy acceptor;

wherein the first fluorophore is the same for all of the different sample fragments of any particular one of the different samples, and is different for each of the different samples;

wherein a combination of the first fluorophore and the second fluorophore is different for each of the different sample fragments of each of the different samples;

wherein the electrophoresis apparatus further comprises:

(2) a light irradiating system which irradiates the sample fragments migrating through the electrophoresis lane with a plurality of exciting lights each having a different wavelength at a plurality of positions simultaneously in the electrophoresis lane such that each of the exciting lights is irradiated at a different one of the positions;

wherein the exciting lights excite the first fluorophore;

wherein the excited first fluorophore transfers energy to the second fluorophore, thereby causing the second fluorophore to emit fluorescence in the electrophoresis lane; and wherein the electrophoresis apparatus further comprises:

(4) a fluorescence detecting system which detects the fluorescence emitted in the electrophoresis lane by the second fluorophore through a plurality of channels; and (5) a sample fragment detecting system which detects the different sample fragments of the different samples from the detected fluorescence based on combinations of the wavelengths of the exciting lights and the channels.

28. A method for analyzing DNA comprising the steps of:

(1) preparing a plurality of different DNA sample groups, each of the DNA sample groups including a plurality of different DNA samples;

(2) labeling each of the DNA samples with an energy donor molecule, and a fluorophore constituting an energy acceptor molecule, the energy donor molecule being the same for all of the different DNA samples of any particular one of the different DNA sample groups, and being different for each of the different DNA sample groups, the fluorophore being different for each of the different DNA samples of any particular one of the different DNA sample groups;

(3) introducing the DNA sample groups into one electrophoresis lane through which the DNA samples migrate;

(4) irradiating the DNA samples migrating through the one electrophoresis lane with a plurality of excitation lasers, each of the excitation lasers having a different wavelength, the excitation lasers exciting the energy donor molecule, the excited energy donor molecule transferring energy to the fluorophore, causing the fluorophore to emit fluorescence in the one electrophoresis lane;

(5) detecting the fluorescence emitted in the one electrophoresis lane by the fluorophore; and (6) detecting the different DNA samples of the different DNA sample groups from the detected fluorescence based on combinations of wavelengths of the fluorescence and wavelengths of the excitation lasers.

* * * * *